United States Patent [19]

Flanagan et al.

[11] Patent Number: 4,938,812

[45] Date of Patent: Jul. 3, 1990

[54] GLYCIDYL AZIDE POLYMER ESTERS

[75] Inventors: Joseph E. Flanagan, Woodland Hills; Edgar R. Wilson, Simi Valley, both of Calif.

[73] Assignee: Rockwell International Corporation, El Segundo, Calif.

[21] Appl. No.: 364,753

[22] Filed: Jun. 12, 1989

[51] Int. Cl.$^5$ ..................... C06B 45/10; C07C 117/00
[52] U.S. Cl. ................................. 149/19.1; 149/19.3; 149/19.5; 149/19.6; 552/12
[58] Field of Search ................. 552/12; 149/19.1, 19.5, 149/19.3, 19.6

[56] References Cited

U.S. PATENT DOCUMENTS

| | | | |
|---|---|---|---|
| 3,441,549 | 4/1969 | Gardiner et al. | 149/19.6 |
| 3,557,181 | 1/1971 | Lakritz et al. | 149/19.6 |
| 3,914,209 | 10/1975 | Petty | 149/19.6 |
| 4,131,499 | 12/1978 | Flanigan | 149/19.3 |
| 4,268,450 | 5/1981 | Frankel et al. | 260/349 |
| 4,379,903 | 4/1983 | Reed, Jr. et al. | 528/55 |
| 4,432,814 | 2/1984 | Witucki et al. | 149/19.1 |
| 4,683,085 | 7/1987 | Frankel et al. | 149/19.1 |
| 4,781,861 | 11/1988 | Wilson et al. | 558/484 |
| 4,795,593 | 1/1989 | Frankel et al. | 149/88 |

Primary Examiner—Edward A. Miller
Attorney, Agent, or Firm—H. Fredrick Hamann; Harry B. Field; David C. Faulkner

[57] ABSTRACT

Glycidyl azide polymer esters for use in insensitive gun and rocket propellants having pendant terminated azide ester groups and a method for producing same.

2 Claims, No Drawings

GLYCIDYL AZIDE POLYMER ESTERS

BACKGROUND OF THE INVENTION

1. Field of the Invention

This invention pertains to energetic plasticizers terminated with ester groups having improved sensitivity for use in insensitive gun and rocket propellants.

2. Description of Related Art

Composite solid propellants may include an oxidizer and metallic fuel together with suitable binders and energetic plasticizers. Other additive components, such as anti-oxidants, burning rate modifiers, wetting agents, and anti-foaming agents may be added to the propellant composition, if desired.

Although the main purpose of the use of plasticizers in propellant formulations is to impart improved low temperature mechanical properties, additional performance benefit is gained by the use of energetic plasticizers. In solid propellants, it is also desirable to utilize an energetic plasticizer which will impart lowered sensitivity to impact, friction and electrostatic discharge which might result in premature ignition or detonation of the propellant. As a consequence, a continuing research effort has been maintained in an attempt to provide a propellant which incorporates a plasticizer which, while enhancing the available energy to be realized from the propellant, simultaneously improves the safe handling and storability of the propellant.

SUMMARY OF THE INVENTION

In accordance with this invention, there is provided a novel family of carboxylic esters which find particular utility as energetic plasticizers for insensitive propellants and the like. Such plasticizers are identified by the following general formula:

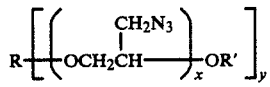

wherein x is an integer from 2 to about 10, y is an integer from 1 to about 4, R is the residue of a mono-hydric alcohol diol. triol or polyol initiator such as ethylene glycol, and R' is the acyl residue of an organic carboxylic acid.

Accordingly, the primary object of this invention is to provide a novel family of glycidyl azide polymer (GAP) carboxylic esters.

Another object of this invention is to provide a novel solid propellant composition having improved sensitivity to impact, friction and electrostatic discharge when utilized in a gun or rocket propellant composition.

Still another object of this invention is to provide a novel family of GAP carboxylic esters that find particular utility as energetic plasticizers for solid propellant compositions.

Yet another object of the present invention is to provide aliphatic polyethers having terminal ester and pendant azidomethyl groups.

These and other objects and features of the present invention will be apparent from the following detailed description.

DESCRIPTION OF THE PREFERRED EMBODIMENT

With the above-mentioned objects in mind, the present invention contemplates the synthesis of a novel family of carboxylic esters and their utilization as energetic plasticizers in gun and solid propellants. A representative plasticizer is prepared by the esterification of a glycidyl azide diol such as described in U.S. Pat. No. 4,268,450 incorporated herein by a reference. The preparation of the novel plasticizers of the present invention is represented by the following synthesis:

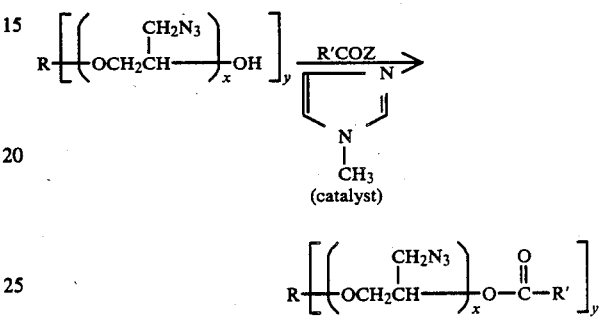

wherein x is an integer from about 2 to about 10, y is an integer from 1 to about 4, R is the hydroxy-free residue of a mono-hydric alcohol, diol. triol or polyol initiator, R' is the residue of a carboxylic acid, and Z is a suitable leaving group such as hydroxyl, halide, or carboxylate.

The esterification reactions can be carried out by reacting the hydroxy terminated glycidyl azide polymer with a carboxylic acid, anhydride or acyl halide in a solvent free or inert solvent system. Basic catalysts such as N-methylimidazole or pyridine can be used to accelerate the reaction if required.

Examples for the preparation of glycidyl azide polymer diacetate (GAPDA) and glycidyl azide polymer di(heptafluorobutyrate)(GAPDHFB) are given in Examples I and II, shown below.

EXAMPLE I

Glycidyl Azide Polymer Diacetate (GAPDA)

To a solution of 100.0g (0.341 eq.) of low molecular weight GAP (equivalent weight of 293.5) and 200 ml of ethylene dichloride was added 183.6 g (1.8 moles) of acetic anhydride. To this mixture was added with good stirring 6 ml of N-methylimidazole catalyst. The reaction temperature rose from 22° to 38° C. After the initial exotherm the reaction mixture was refluxed for 3 hrs, cooled, drowned in 1l of water, and extracted with 300 ml of methylene chloride. The organic layer was separated, washed with 2×1l water and 1 l of 5% sodium bicarbonate solution, dried over anhydrous magnesium sulfate, and passed through a 100 g column of chromatographic grade silica gel. Concentration of the solution gave 97.6 g (75.4%) of light yellow liquid with properties as shown in Table I.

EXAMPLE II

Glycidyl Azide Polymer Diheptafluorobutyrate (GAPHDFB)

To Glycidyl Azide Polymer diol 9.2 g (0.016 m) was added 26.04 g of perfluorobutyric acid. This mixture was heated to 75-80° C. with stirring for 5 hours. The reaction mixture was then dumped into water and 25 ml of methylene chloride was added. The organic phase was separated and re-washed with dilute sodium bicarbonate solution to remove residual acid. The product solution was dried over anhydrous magnesium sulfate and then passed through a 10 g column of silica gel which removed most of the color. The recovered solution was stripped to yield 6.4 g of pale yellow oil. Impact sensitivity was found to be greater than 100 in-lb, sensitivity to electrostatic discharge was found to be greater than 12 but less than 18 Joules, and friction sensitivity was determined to be 36 kg using a Julius Peters friction test apparatus.

that within the scope of the appended claims the invention may be practiced other than specifically described.

What is claimed is:

1. A propellant consisting essentially of a binder, oxidizer, and fuel and an energetic plasticizer having the following general formula:

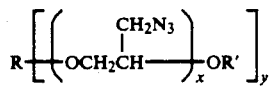

wherein x is an integer from 2 to about 10, y is an integer from 1 to about 4, R is the residue of a mono-hydric

TABLE I

| PROPERTIES OF GAPDA | |
|---|---|
| NAME: | GAP DIACETATE |
| STRUCTURE: | $CH_3OC{-}[OCHCH_2(CH_2N_3){-}]_2{-}OCH_2CH_2O{-}[CH_2CHO(CH_2N_3){-}]_3COCH_3$ |
| FORMULA: | $C_{21}H_{35}N_{15}O_9$ |
| MOLECULAR WEIGHT: | 641 |
| ELEMENTAL ANALYSES: | C    H    N |
| Calculated: | 39.31    5.46    32.76 |
| Found: | 39.08    5.50    32.69 |
| INFRARED SPECTRUM: | $N_3$ (2100 cm$^{-1}$), C=O (1745 cm$^{-1}$) |
| APPEARANCE: | Light Yellow Liquid |
| REFRACTIVE INDEX: | 1.4920 @ 24 C. |
| DENSITY: | 1.235 @ 24C. |
| FREEZING POINT: | Not Detectable to −90 C. |
| DSC: | Onset 229 C. |
| WEIGHT LOSS: | 0.5% after 24 hrs @ 74 C. (TMETN-3.0%) |
| IMPACT SENSITIVITY: | 160 in-lb |
| FRICTION SENSITIVITY: | 10.8 Kg |
| $\Delta H_f$(Estimated): | −9 Kcal/mole |

Obviously, numerous variations and modifications may be made without departing from the present invention. Accordingly. it should be clearly understood that the form of the present invention described above is illustrative only and is not intended to limit the scope of the present invention. It is therefore to be understood alcohol, diol, triol or polyol and R' is the acyl residue of an organic carboxylic acid.

2. A composition of matter glycidyl azide polymer diheptafluorobutyrate.

* * * * *

UNITED STATES PATENT AND TRADEMARK OFFICE
CERTIFICATE OF CORRECTION

PATENT NO. : 4,938,812

DATED : July 3, 1990

INVENTOR(S) : Flanagan et al.

It is certified that error appears in the above-identified patent and that said Letters Patent is hereby corrected as shown below:

Column 4, Claim 1, Line 12, the word "inleger" should be --integer--.

Column 4, Claim 1, Line 37, insert "initiator," between the words "polyol" and "and".

Signed and Sealed this

Twentieth Day of August, 1991

Attest:

HARRY F. MANBECK, JR.

Attesting Officer

Commissioner of Patents and Trademarks